United States Patent [19]
Suzuki et al.

[11] Patent Number: 5,804,394
[45] Date of Patent: Sep. 8, 1998

[54] REAGENT FOR MEASURING CREATINE KINASE ACTIVITY AND MEASURING METHOD THEREOF

[75] Inventors: Tadao Suzuki; Tomoko Kamei, both of Kyoto; Mihoko Era, Soraku-gun; Hiroyuki Tsubota, Chiba, all of Japan

[73] Assignees: Unitika Ltd.; Iatron Laboratories, Inc., both of Japan

[21] Appl. No.: 138,076

[22] Filed: Oct. 20, 1993

Related U.S. Application Data

[63] Continuation-in-part of Ser. No. 13,989, Feb. 5, 1993, abandoned, which is a continuation of Ser. No. 870,099, Apr. 16, 1992, abandoned, which is a continuation of Ser. No. 334,864, Apr. 6, 1989, abandoned.

[30] Foreign Application Priority Data

Apr. 6, 1988 [JP] Japan ................................ 63-86163

[51] Int. Cl.$^6$ ....................... G01N 33/573; A61K 39/395
[52] U.S. Cl. .............................. 435/7.4; 435/7.1; 435/17; 435/172.2; 435/810; 436/524; 436/538; 436/547; 436/548; 436/811; 530/388.1; 530/388.26; 530/391.1; 935/110
[58] Field of Search ............... 435/7.1, 7.4, 7.6, 435/240.27, 17, 172.2, 810; 436/524, 528, 531, 538, 547, 548, 811, 815; 530/387.1, 388.1, 388.26, 389.1, 391.1; 935/110

[56] References Cited

U.S. PATENT DOCUMENTS

| | | | |
|---|---|---|---|
| 4,067,775 | 1/1978 | Wurzburg et al. | 435/7.4 |
| 4,900,662 | 2/1990 | Shah et al. | 435/7.4 |
| 5,202,234 | 4/1993 | Shah et al. | 435/7.4 |

FOREIGN PATENT DOCUMENTS

| | | |
|---|---|---|
| 0178113 | 4/1986 | European Pat. Off. . |
| 0227440 | 7/1987 | European Pat. Off. . |

OTHER PUBLICATIONS

George et al., "The Journal of Biological Chemistry", 259(4) 2667–2674 (Feb. 25, 1984).
Kohler et al., "Nature", 256 495–497 (Aug. 7, 1975).
Suzuki et al., Derwent Abstracts, C88–038542.
Buckel et al., "Chemical Abstracts", 106 208725e (1987) p. 175.
"Chemical Abstracts", 109, p. 508, Abstract No. 36622n (1988).
"Chemical Abstracts", 109, p. 499, Abstract No. 5160f (1988).
"Biol. Abst.", 33(6), p. 986 (1987) Abst. No. RRM 33073450.

*Primary Examiner*—Laurie A. Scheiner
*Attorney, Agent, or Firm*—Wenderoth, Lind & Ponack

[57] ABSTRACT

The present invention provides such a measuring method of the CK isoform and a reagent therefor. Accordingly, the present invention provides a reagent for measuring creatine kinase (CK) activity comprising an antibody, wherein said antibody inhibits CK-$M_T$ subunit, but does not inhibit CK-$M_S$ subunit.

The present invention also provides a method for measuring CK activity comprising determining an inhibition of CK of body fluids using a reagent for measuring CK activity, wherein said reagent comprises an antibody which inhibits CK-$M_T$ subunit, but does not inhibit CK-$M_S$ subunit.

5 Claims, 4 Drawing Sheets

REAGENT FOR MEASURING CREATINE KINASE ACTIVITY AND MEASURING METHOD THEREOF

This is a Continuation-in-part of Ser. No. 08/013,989, filed Feb. 5, 1993, now abandoned which is a Continuation of now-abandoned application Ser. No. 07/870,099, filed Apr. 16, 1992, now abandoned which is a Continuation of now-abandoned application Ser. No. 07/334,864, filed Apr. 6, 1989.

FIELD OF THE INVENTION

The present invention relates to a reagent for measuring creatine kinase isoforms in body fluids and the method of measurement thereof.

BACKGROUND OF THE INVENTION

Creatine kinase (CK) catalyzes the following reaction:

Measurement of CK activity in body fluids, especially in serum, is very important for the diagnosis of skeletal and myocardiac muscle disorder, especially, acute myocardial infarction (AMI). CK consisits of two subunits, M (muscle type) and B (brain type), and three kinds of isoenzymes are present in cytoplasm, CK-MM, MB and BB. In particular, the separate measurement of CK-MB is recommended for specific diagnosis of myocardial infarction.

It has been elucidated that there are several post-translational isoforms of CK-MM and MB isoenzymes (George S., et al., J. Biol. Chem., 259, 2667–74 (1984). M subunit originally present in tissue, for example in cardiac muscle, is "tissue type M subunit (designated $M_T$)." Once $M_T$ subunits in CK-MM or MB are released into blood stream, carboxypeptidase in plasma cleaves C-terminal lysine of the $M_T$ subunits, generating "serum type M subunit (designated $M_S$)". Thus, CK-MM is converted from MM3 (tissue type, $M_T M_T$) via MM2 (hybrid type $M_T M_S$) to MM1 (serum type, $M_S M_S$).

It has been also clarified that the measurement of CK isoforms is a good index for earlier diagnosis of AMI and earlier detection of reperfusion after treatment of colonary thrombolysis. For example, it was reported that the ratio of MM3 to MM1 (MM3/MM1) is approximately 0.3 in healthy subjects, however, the ratio rises to 2.0, 3 to 6 hours after onset of AMI (Hashimoto H., et al., Circulation, 71, 366 (1985). Jaffe, et al. also reported (Circulation, 74, 105–9 (1986) that 86% of the ratio in the first serum samples collected after onset from AMI patients exceeded its reference interval, on the other hand, the mean of total CK or CK-MB, those of which are conventional markers for diagnosis of AMI, still remained in their reference intervals.

Accordingly, the measurement of CK isoforms is very useful for the earlier diagnosis of AMI, compared with conventional AMI marker such as total CK activity and CK-MB. Earlier diagnosis of AMI makes it possible to treat AMI patients earlier with coronary thrombolysis or angioplasty.

The methods for the measurement of CK isoforms which have been reported are electrophoresis, isoelectric focusing, chromatofocusing, and liquid chromatography. Those methods are complicated, time-consuming, difficult to automate, and thus inadequate for emergent and routine assay.

Immunoassay is widely used in clinical chemistry field, and very excellent method because of its high sensitivity and specifity. Shah et al. showed immunoassay of CK isoforms using isoforms specific antibodies (U.S. Pat. No. 4,900,662). This method, however, requires long incubation time and separation and washing steps of solid phase from liquid phase, indicating that the method is complicated, laborious and unsuitable for emergency assay.

Immunoinhibition assay is also used in clinical laboratories. This method employs antibodies that inhibit part of enzyme activity such as particular isoenzymes. This method is being applied to the measurement of CK-MB isoenzyme using antibodies that inhibit CK-M (both $M_T$ and $M_S$). In the assay, after all M subunit activity are inhibited by the antibodies, remaining B subunit activity is then measured (Japanese Patent Publication 19239/1981 and 20274/1983). The immonoinhibition assay requires no separation procedures. The assay completes in short time and is easily automated, indicating that the assay is adequate for emergent and routine measurement. Immunoinhibition assay, however requires very specific antibodies. Antibodies used for immunoinhibition assay must have the ability not only in distinguishing isoenzymes or isoforms from each other but also in inhibiting particular enzyme activity. Generally, the antibodies against enzymes do not have either the distinguishing or inhibiting ability. The antibodies disclosed in the U.S. Pat. No. 4,900,662 cannot inhibit the enzymatic activity, meaning that they cannot be used in the immonoinhibition assay of CK isoform. The antibodies disclosed in the patents 19239 and 20274 cannot distinguish CK-$M_T$ subunit from CK-$M_S$. They also cannot be used in the immunoinhibition assay.

Therefore, a faster and easier method for the measurement of CK isoforms is eagerly required. The present invention provides the method for the measurement of CK isoform by immunoinhibition assay.

SUMMARY OF THE INVENTION

The present invention provides the antibodies that can inhibit CK-$M_T$ subunit but not MB, the method for measurement of CK isoform and a reagent therefor. Accordingly, the present invention provides a reagent for measuring creatine kinase (CK) activity comprising an antibody, wherein said antibody inhibits creatine kinase (CK) $M_T$ subunit, but does not inhibit creatine kinase (CK) $M_S$ subunit.

The present invention also provides a method for measuring creatine kinase (CK) activity comprising determining an inhibition of creatine kinase (CK) of body fluids using a reagent for measuring creatine kinase (CK) activity, wherein said reagent comprises an antibody which inhibits creatine kinase (CK) $M_T$ subunit, but does not inhibit creatine kinase (CK) $M_S$ subunit. DETAILED DESCRIPTION OF THE INVENTION The antibody of the present invention can be either polyclonal or monoclonal, but a monoclonal antibody is preferred. Physicochemical characteristics of the antibody are shown as follow;

(1) Action
  The antibody acts on creatine kinase (CK) to raise an antigen-antibody reaction, then inhibits creatine kinase (CK) $M_T$ subunit activity.
(2) Reaction specificity
  The antibody inhibits only M subunit of creatine kinase (CK) $M_T$ subunit, but does not inhibit $M_S$ subunit.
(3) Optimum pH
  6 to 9
(4) Suitable pH range
  3 to 11

(5) Measuring method of potency
Measured by a dilution rate which is detected from the measurement of inhibition.
(6) Suitable temperature range for action
0° to 40° C.
(7) Condition of inactivation
The antibody is inactivated at 100° C. for 30 minutes.
(8) Molecular weight
130,000 to 210,000

For obtaining the monoclonal antibody, a hybridoma cell strain which can produce a monoclonal antibody inhibiting creatine kinase (CK) $M_T$ activity is necessary. Such a hybridoma cell strain has the following cytological characteristics;

(1) Derivation
Fused cells of lymphocytes producing anti-CK-M antibody and myeloma cells.
(2) Shape
The fused cells have similar shape to myeloma cells. They have a size of 10 to 20 micrometer.
(3) Function
They constantly produce monoclonal antibodies inhibiting CK-$M_T$ activity which recognize one antigenic determinant.
(4) Growth ability
They show proliferation ability similar to myeloma cells. Thus, they proliferate about ten times in number for 72 hours.
(5) Storage stability
They are stored for a long period of time at a temperature of not more than −120° C.
(6) Optimum proliferation conditions
37° C., pH 7.2
(7) Proliferation range
32° to 42° C., pH 6.5 to 7.8

For obtaining such cell strain, hybridomas which produce a monoclonal antibody inhibiting CK-$M_T$ activity are obtained by, for example, a method described in Japanese Patent Application Ser. No. 191899/1986, from which some hybridomas which do not inhibit $M_S$ subunit are selected in a similar manner mentioned above.

As mentioned above, hybridomas producing antibodies which inhibit CK-$MM_3$, but do not inhibit CK-$MM_1$ are obtained. One of hybridomas which is actually obtained by the above mentioned method is deposited on Jan. 26, 1988 at Fermentation Research Institute Agency of Industrial Science and Technology, Ibaraki-ken, Japan to assign a number of FERM P-9839, and was deposited under the Budapest Treaty as BP-2280 at the Fermentation research Institute, Agency of Industrial Science and Technology, 1–3, Higashi 1-Chome, Tsukaba-shi, Ibaraki-ken 305, Japan. These hybridomas are named CKH-5 and can be permanently stored at −120° C.

The hybridomas are cultured and an antibody are obtained therefrom. The obtaining method of the antibody is known to the art, especially a method described in Japanese Patent Application Ser. No. 191899/1986. The obtained antibodies may be used intact. They may be treated with proteolytic enzymes, such as pepsin, papain and the like to form Fab, Fab', F(ab')$_2$ fragments.

The reagent for measuring creatine kinase activity is prepared and used as generally described in Japanese Patent Publications (examined) 19239/1981 and 20274/1983 and Japanese Patent Application Ser. No. 191899/1986. For example, the reagent is generally composed of two packages. The first package generally contains 0.1 to 40 unit/ml of glucokinase (GlcK) or hexokinase (HK), 0.1 to 40 unit/ml of glucose-6 phosphate dehydrogenase (G6PDH), 0.001 to 5 mg/ml of M subunit inhibiting antibody (Ab), 0.1 to 20 mM of adenosine diphosphate (ADP), 0.05 to 20 mM of nicotinamide adenine dinucleotide (NAD$^+$) or nicotinamide adenine dinucleotide phosphate (NADP$^+$), 1 to 200 mM of glucose, 0.2 to 20 mM of adenosine monophosphate (AMP), 0.001 to 0.1 mM of diadenosine pentophosphate (Ap5A), 0.5 to 50 mM of N-acetylcysteine (NAC) or another thiol compound, 0.5 to 30 mM of magnesium salts (e.g. magnesium acetate), 0.5 to 50 mM of sodium azide, 0.1 to 20 mM of ethylenediamine tetraacetate (EDTA) and 5 to 50 mM of a buffer solution (pH 6.7). The second reagent contains 2 to 70 mM of creatine phosphate (CrP), 0.5 to 50 mM of sodium azide and 5 to 500 mM of a buffer solution. Preferably, in the first reagent, Glck or HK is present in an amount of 0.2 to 20 unit/ml, G6PDH is in an amount of 0.2 to 20 unit/ml, Ab is 0.005 to 2 mg/ml, ADP is 0.2 to 10 mM, NAD$^+$ or NADP$^+$ is 0.1 to 10 mM, glucose is 2 to 100 mM, AMP is 0.5 to 15 mM, Ap5A is 0.002 to 0.050 mM, NAC is 2 to 30 mM, magnesium salts are 1 to 15 mM, sodium azide is 1 to 30 mM, EDTA is 0.2 to 10 mM and the buffer solution (pH 6.7) is 10 250 mM. In the second reagent, preferably CrP is present in an mount of 5 to 40 mM, sodium azide is in an amount of 1 to 30 mM and the buffer solution is 10 to 250 mM.

As a measuring method, 0.5 ml of the first reagent is mixed with 0.001 to 0.02 ml of an enzyme solution (or serum) containing creatine kinase and kept at 25° to 37° C. for 5 to 10 minutes. Then, 0.125 ml of the second reagent is added to it and the residual creatine kinase activity is measured by an absorption change of 340 nm using a spectrometer. Thereafter, as a control, the first reagent which does not contain the antibody is added to the enzyme solution (or serum) and measured in a same manner as mentioned above. An inhibition rate is given by the following formula from the residual creatine kinase (CK) activity and the control creatine kinase (CK) activity;

$$\text{Inhibition rate (\%)} = \frac{\text{Control activity} - \text{Residual activity}}{\text{Control activity}} \times 100$$

The antibody of the present invention does not inhibit creatine kinase (CK)-$M_S$ subunit, but inhibits creatine kinase (CK)-$M_T$ subunit. $M_T$ subunit of creatine kinase which has been released from the heart by myocardial infarction is modified with carboxypeptidase of blood. Thus, CK-$M_TM_T$ ($MM_3$) is modified through $M_TM_S(MM_2)$ to $M_SM_S(MM_1)$, and CK-MB is modified to $M_S(MB_1)$ with the passage of time. A large amount of creatine kinase just after released from the heart is modified very little so as to obtain a high inhibition. As proceeding the modification, the inhibition is lowered. Accordingly, by measuring an inhibition with the reagent of the present invention, myocardial infarction is early examined and a time when a patient fall in disease is estimated.

EXAMPLES

The present invention will be illustrated by the following Examples which are not to be construed as limiting the present invention to their details.

Example 1

An emulsion mixture of 50 microgram of pig CK-MM with complete Freund adjuvant (available from Nakarai Chemical Company) in a ratio of 1:1 was administered to 8 weeks mouse Balb/c (available from Nippon Clea Company). After three weeks, 50 microgram of pig ck-MM was intravenously injected. It was then fused with mouse myeloma X63.6.5.3 by a method by Oi, V. T., Selected Methods in Cellular Immunology, p. 351, W. H. Freeman and Co., 1980 and hybridoma grew in 54 wells/96 wells. The supernatant was added to a reagent for measuring creatine kinase (CK) activity of the following Reference Example 2 and an inhibition of CK-MM was measured with respect to $CK-MM_3$ and $CK-MM_1$ to select antibodies which does not inhibit $Ck-MM_1$ but inhibits $CK-MM_3$. The selected strain was cloned by a limit dilution method to obtain a hybridoma CKH-5 (BP-2280) of monoclone. The CKH-5 shows the same cytological properties as mentioned before.

The hybridoma CKH-5 was cultured on RPM11640 culture medium containing 10% fetal bovine serum to a cell number of $2\times10^6$/ml, 300 ml of which was then subjected to centrifugal separation to collect the supernatant. It was then fractionated with ammonium sulfate to obtain crude antibody fraction, and absorbed to Protein A Cephalose (pH 8.0) after dialyzing. The absorbed fraction was eluted with a citric acid buffer solution to obtain a monoclonal antibody (CKA-5) of 3.2 mg.

Reference Example 1

The antibody was added to reagents for measuring creatine kinase (CK) activity to determine inhibition of $CK-MM_3$, $MM_2$ and $MM_1$ in serum separated by a chromatofocusing.

The first reagent was prepared by mixing 1.4 unit/mi of GlcK derived from *Bacillus stearothermophilus* (available from Seikagaku Kogyo Co., Ltd.), 1.2 unit/ml of G6PDH derived from *Leuconostoc mesenteroides* (available from Oriental Yeast Co., Ltd.), 1.2 mM of ADP, 0.75 mM of NADP, 25 mM of glucose, 6.25 mM of AMP, 125 micro M of Ap5A, 12.5 mM of N-acetylcystein, 12.5 mM of magnesium acetate, 10 mM of sodium azide, 2.5 mM of EDTA and 150 mM of an imidazole-acetate buffer solution (pH 6.7). The second reagent was prepared by mixing 100 mM of CP, 10 mM of sodium azide and 25 mM of a Tris-acetate buffer solution (pH 8.5).

The monoclonal antibody CKA-5 inhibiting CK-M activity was added to the first reagent and $CK-MM_3$, then $MM_2$ or $MM_1$ was added to 0.5 ml of the mixture. It was then charged in a cell having a light length of 1 cm and incubated for 15 minutes. Next, 0.125 ml of the second reagent was added and the residual CK activity was measured by an absorption of 340 nm using a spectrometer which was kept at 30° C. As control, $CK-MM_3$, $MM_2$ or $MM_1$ was added to the reagent which does not contain the antibody, and subjected to a same measuring. The result is shown in Table 1.

TABLE 1

| | Inhibition activity of CKA-5 | | |
|---|---|---|---|
| Isoform | Activity with no antibody (u/l) | Activity with antibody (u/l) | Inhibition (%) |
| $CK-MM_3$ | 221 | 1 | 100 |
| $CK-MM_2$ | 210 | 101 | 52 |
| $CK-MM_1$ | 197 | 195 | 1 |

Note: the values are an average of three samples.

As shown in Table 1, CKA-5 does not inhibit $CK-MM_1$ of serum type, but inhibits $CK-MM_3$ of tissue type. It also inhibits a half of $MM_2$ of hybrid type. Thus, CKA-5 does not inhibit $M_T$ subunit, but inhibits $M_S$ subunit, and is inside of the physicochemical characteristics.

Reference Example 2 and Comparative Example 1

CK-MM (800U/1) purified from cardiac muscles was added to blood plasma and incubated at 37° C. Inhibition of CK-MM by CKA-5 was determined with time as generally described in Reference Example 2. A diagnostic reagent for measurement of CK-MB (CK-MB kit) which contains CK-MM inhibiting antibody (Boehringer Mannheim Company) was employed as a comparative example and inhibition was measured. The result is shown in Table 2.

TABLE 2

| Change with time of inhibition by CKA-5 | | |
|---|---|---|
| Incubation time (hours) | Inhibition by CKA-5 (%) | Inhibition by CK-MB kit (%) |
| 0 | 97.3 | 100 |
| 1 | 57.6 | 100 |
| 2 | 38.9 | 100 |
| 3 | 23.5 | 100 |
| 4 | 16.1 | 97.0 |
| 5 | 8.2 | 96.7 |
| 6 | 0 | 100 |

As the purified $CK-MM(MM_3)$ is modified by carboxy peptitase N in blood plasma to $MM_2$ and $MM_1$, inhibition of CK-MM by CKA-5 reduces with time and 6 hours later there is no inhibition. This is corresponded to the change of isoform. On the other hand, the inhibition of CK-MM by CK-MB kit does not change after 6 hours and therefore this can not traces the change of isoform.

Example 2 and Comparative Example 2

As generally described in Reference Example 2, the CK activity and inhibition by CKA-5 of the serum from patient A who had onset of myocardial infarction was determined with time. For a comparison, the activity of CK-MB was determined using a reagent for CK-MB measurement kit which contains a CK-MM inhibiting antibody. The result is shown in FIG. 1 and FIG. 2. As shown in the figures, the inhibition by CKA-5 shows a peak after 6 hours from the onset, but CK-MB which has been used for a diagnosis of myocardial infarction shows a peak after 21 hours from the onset. Accordingly, it is very clear that the measurement of the inhibition by CKA-5 is very useful for an early diagnosis of myocardial infarction.

Example 3 and Comparative Example 3

As generally described in Example 1, the CK activity and inhibition by CKA-5 of the serum from patient B who had a fit of myocardial infarction was determined with time. For a comparison, the activity of CK-MB was determined as generally described in Comparative Example 2. The result is shown in FIG. 3 and FIG. 4. As shown in the figures, the inhibition by CKA-5 shows a peak after 6 hours from the onset, but that of CK-MB which has been used for a diagnosis of myocardial infarction shows a peak after 16 hours from the onset. Accordingly, it is very clear that the measurement of the inhibition by CKA-5 is very useful for an early diagnosis of myocardial infarction.

Figure 1:
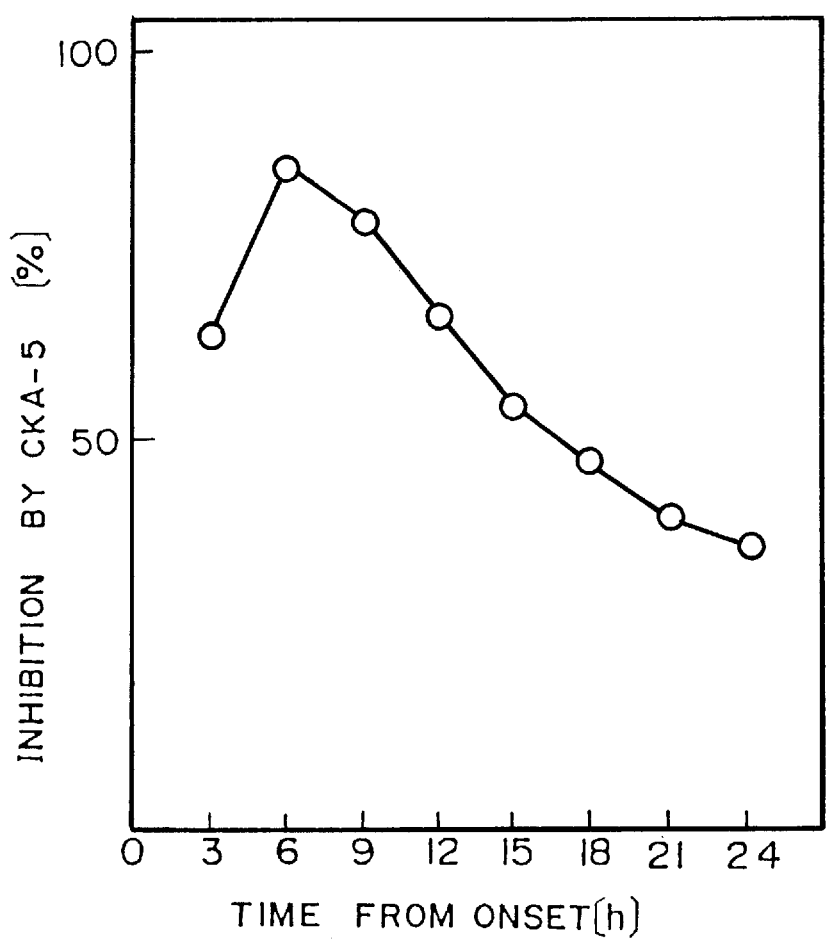
FIGS. 1 and 3 show a relation of an inhibition by CKA-5 with time after onset of myocardial infarction.
Figure 2:
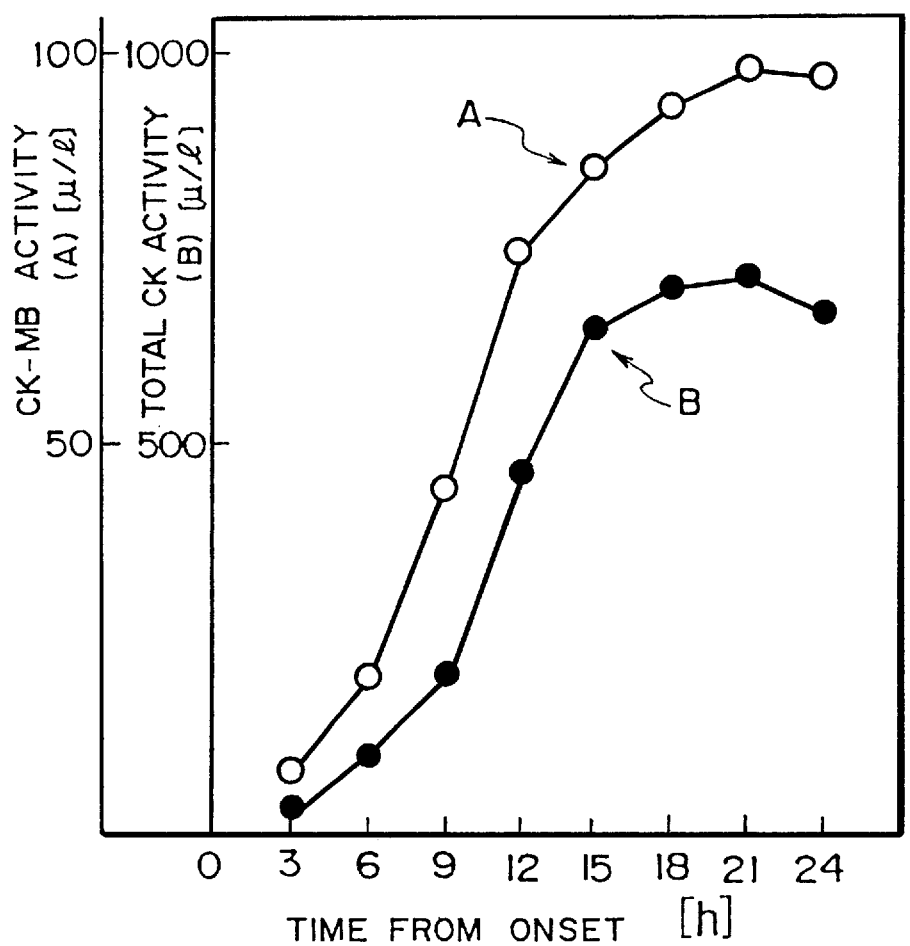
FIGS. 2 and 4 show a relation of a total CK activity (A) and CK-MB activity (B) with time after onset of myocardial infarction.
Figure 3:
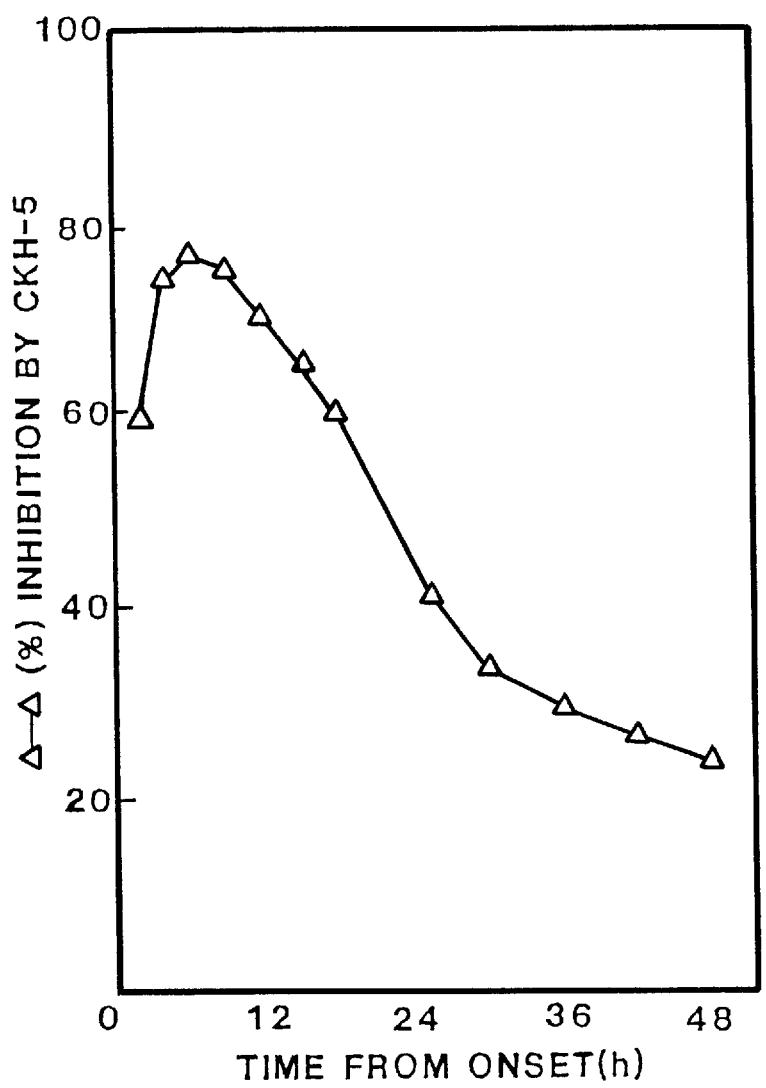
Figure 4:
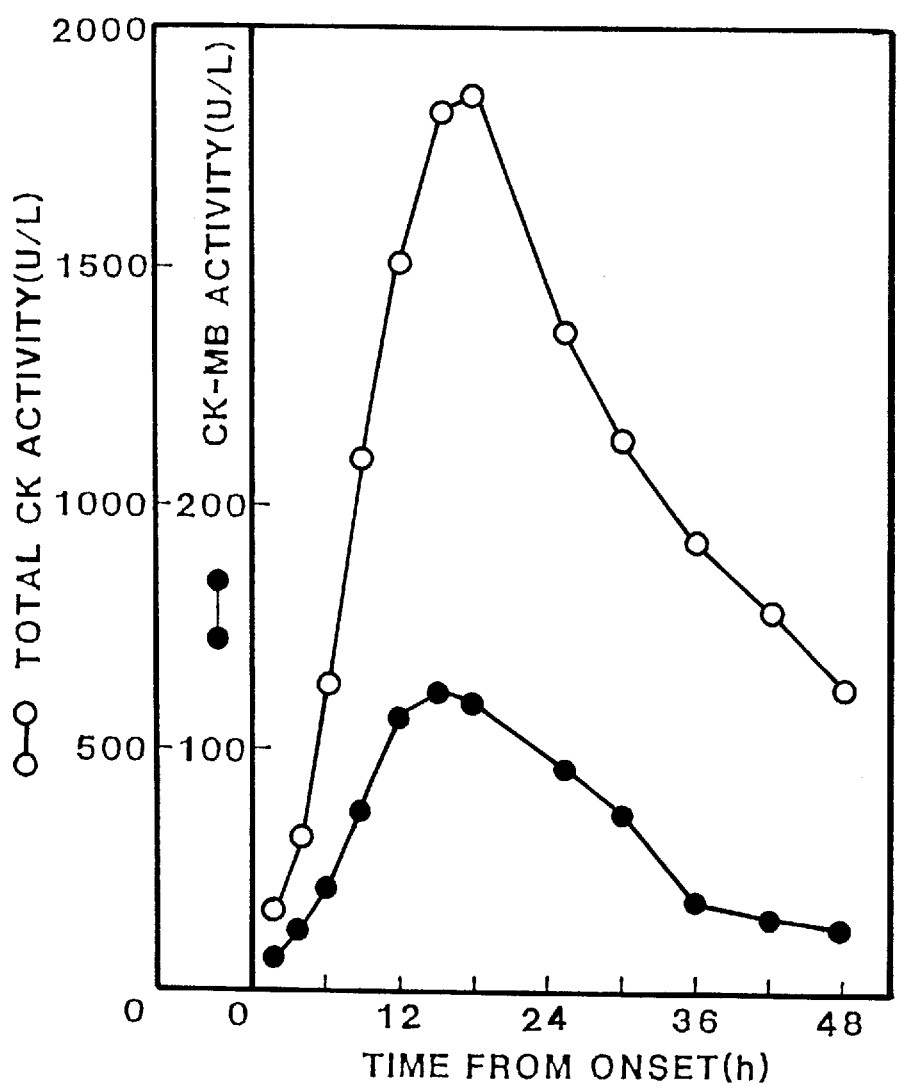

What is claimed is:

1. Anti CK-$M_T$ monoclonal antibody which can inhibit CK-$M_T$ subunit activity, but not inhibit CK-$M_S$ subunit activity, said antibody obtained from hybridoma cell line BP-2280.

2. A method for measuring creatine kinase activity comprising determining an inhibition of creatine kinase of body fluids using a reagent for measuring creatine kinase activity, wherein said reagent comprises a monoclonal antibody which inhibits creatine kinase $M_T$ subunit, but does not inhibit creating kinase $M_S$ subunit, said antibody obtained from hybridoma cell line BP-2280.

3. A reagent for measuring creatine kinase activity comprising a monoclonal antibody, said antibody obtained from hybridoma cell line BP-2280, wherein said antibody inhibits creatine kinase $M_T$ subunit, but does not inhibit creatine kinase $M_S$ subunit.

4. The reagent according to claim 3 being composed of two packages, one of which comprises 0.1 to 40 unit/ml of glucokinase (GlcK) or hexokinase (HK), 0.1 to 40 unit/ml of glucose-6 phosphate dehydrogenase (G6PDH), 0.001 to 5 mg/ml of said creatine kinase $M_T$ subunit inhibiting monoclonal antibody (Ab), 0.1 to 20 mM of adenosine diphosphate (ADP), 0.05 to 20 mM of nicotinamide adenine dinucleotide (NAD$^+$) or nicotinamide adenine dinucleotide phosphate (NADP$^+$), 1 to 200 mM of glucose, 0.2 to 20 mM of adenosine monophosphate (AMP), 0.001 to 0.1 mM of diadenosine pentophosphate (Ap5A), 0.5 to 50 mM of N-acetylcysteine (NAC) or another thiol compound, 0.5 to 30 mM of magnesium salts, 0.5 to 50 mM of sodium azide, 0.1 to 20 mM of ethylenediamine tetraacetate (EDTA) and 5 to 50 mM of a buffer solution (pH 6.7), and the other reagent comprises 2 to 70 mM of creatine phosphate (CrP), 0.5 to 50 mm of sodium azide and 5 to 500 mM of a buffer-solution.

5. The method according to claim 4 wherein said reagent is composed of two packages, one of which comprises 0.1 to 40 unit/ml of glucokinase (GlcK) or hexokinase (HK), 0.1 to 40 unit/ml of glucose-6 phosphate dehydrogenase (G6PDH), 0.001 to 5 mg/ml of said creatine kinase $M_T$ subunit inhibiting monoclonal antibody (Ab), 0.1 to 20 mM of adenosine diphosphate (ADP), 0.05 to 20 mM of nicotinamide adenine dinucleotide (NAD$^+$) or nicotinamide adenine dinucleotide phosphate (NADP$^+$), 1 to 200 mM of glucose, 0.2 to 20 mM of adenosine monophosphate (AMP), 0.001 to 0.1 mM of diadenosine pentophosphate (Ap5A), 0.5 to 50 mM of N-acetylcysteine (NAC) or another thiol compound, 0.5 to 30 mM of magnesium salts, 0.5 to 50 mM of sodium azide, 0.1 to 20 mM of ethylenediamine tetraacetate (EDTA) and 5 to 50 mM of a buffer solution (pH 6.7), and the other reagent comprises 2 to 70 mM of creatine phosphate (CrP), 0.5 to 50 mM of sodium azide and 5 to 500 mM of a buffer solution.

* * * * *